(12) United States Patent
Bogosian et al.

(10) Patent No.: US 6,617,130 B1
(45) Date of Patent: Sep. 9, 2003

(54) DNA CONSTRUCT FOR REGULATING THE EXPRESSION OF A POLYPEPTIDE CODING SEQUENCE IN A TRANSFORMED BACTERIAL HOST CELL

(75) Inventors: Gregg Bogosian, Clarkson Valley, MO (US); Julia P. O'Neil, St. Louis, MO (US); Katherine C. Terlesky, Charlottesville, VA (US)

(73) Assignee: Monsanto Technology LLC, St. Louis, MI (US)

( * ) Notice: Subject to any disclaimer, the term of this patent is extended or adjusted under 35 U.S.C. 154(b) by 0 days.

(21) Appl. No.: 09/539,746

(22) Filed: Mar. 31, 2000

Related U.S. Application Data
(60) Provisional application No. 60/127,449, filed on Apr. 1, 1999.

(51) Int. Cl.[7] .......................... C12P 21/06; C12N 1/20; C12N 15/70
(52) U.S. Cl. ............... 435/69.1; 435/320.1; 435/252.3; 435/252.33; 536/23.1; 536/24.1; 536/24.2
(58) Field of Search ................ 536/23.1, 24.1, 536/24.2; 435/320.1, 69.1, 252.33, 252.3

(56) References Cited

U.S. PATENT DOCUMENTS

| | | |
|---|---|---|
| 4,551,433 A | 11/1985 | DeBoer |
| 4,704,362 A | 11/1987 | Itakura et al. |
| 4,861,868 A * | 8/1989 | Krivi .......................... 530/399 |
| 4,912,046 A | 3/1990 | Henner et al. |
| 5,162,216 A | 11/1992 | Scandella et al. |
| 5,221,619 A | 6/1993 | Itakura et al. |
| 5,516,693 A | 5/1996 | Vaeck et al. |
| 5,518,897 A | 5/1996 | Stevens, Jr. et al. |
| 5,583,013 A | 12/1996 | Itakura et al. |
| 6,194,168 B1 * | 2/2001 | Gentz et al. ............... 435/69.1 |

FOREIGN PATENT DOCUMENTS

| | | |
|---|---|---|
| EP | 0067540 A2 | 12/1982 |
| EP | 0108045 A1 | 5/1984 |
| EP | 0971034 A1 | 1/2000 |
| WO | WO 98/22590 | 5/1998 |

OTHER PUBLICATIONS

No additional references are cited by the Examiner.*

Ma et al., Analysis of the Promoter and Regulatory Sequences of an Oxygen–Regulated bch Operon in *Rhodobacter capsulatus* by Site–Directed Mutagenesis, *Journal of Bacteriology*, 175(7): 2037–45 (1993).

Schneider and Haselkorn, Characterization of Two Early Promoters of Cyanophage N–1; *Virology* 167: 150–155 (1988).

* cited by examiner

*Primary Examiner*—David Guzo
*Assistant Examiner*—David A. Lambertson
(74) *Attorney, Agent, or Firm*—George R. Beck; Howrey Simon Arnold & White, LLP

(57) ABSTRACT

A heterologous polypeptide is expressed under the control of a DNA construct containing a promoter region derived from a cyanophage or cyanobacteria promoter. In one embodiment, such a promoter region is operably linked to an operator region derived from an operator native to the host cell. In another embodiment, the operator region is positioned upstream of the promoter region.

26 Claims, 12 Drawing Sheets

```
EcoRI
    |
    GAATTCTACTGTATGAGCATACAGTAACGCTTGACAACCGATATATTATTCACTTAATATA
1   ------+---------+---------+---------+---------+---------+  60
    CTTAAGATGACATACTCGTATGTCATTGCGAACTGTTGGCTATAAATAAGTGAATTATAT

AscI
                   |
    TAAATATCAACTGAGGCGCGCCTAAAAAGGGTATCGACAATGTATCGCGATTTAAATAAG
61  ------+---------+---------+---------+---------+---------+ 120
    ATTTATAGTTGACTCCGCGCGGATTTTTCCCATAGCTGTTACATAGCGCTAAATTTATTC

GAGGAATAACATATGTTCCCAGCCATGTCCTTGTCCGGCCTGTTTGCCAACGCTGTGCTC
121 ------+---------+---------+---------+---------+---------+ 180
    CTCCTTATTGTATACAAGGGTCGGTACAGGAACAGGCCGGACAAACGGTTGCGACACGAG
                     MetPheProAlaMetSerLeuSerGlyLeuPheAlaAsnAlaValLeu
```

FIG. 2-A

```
      BlpI
       |
      CGGGGCTCAGCACCTGCATCAGCTGGCTGCTGACACCCTTCAAAGAGTTTGAGCGCACCTAC
181   ------+---------+---------+---------+---------+---------+   240
      GCCCGAGTCGTGGACGTAGTCGACCGACGACTGTGGAAGTTTCTCAAACTCGCGTGGATG
      ArgAlaGlnHisLeuHisGlnLeuAlaAlaAspThrPheLysGluPheGluArgThrTyr  -
                                               EKBGH
                                         ◄──────────────

ATCCCGGAGGGACACAGAGATACTCCATCCAGAACACCCAGGTTGCCTTCTGCTTCTCTGAA
241   ------+---------+---------+---------+---------+---------+   300
      TAGGGCCTCCCTGTCTCTATGAGGTAGGTCTTGTGGGTCCAACGGAAGACGAAGAGACTT
      IleProGluGlyGlnArgTyrSerIleGlnAsnThrGlnValAlaPheCysPheSerGlu  -
         ─────────

ACCATCCCGGCCCCCACGGGCCAAGAATGAGGCCCAGCAGAAATCAGACTTGGAGCTGCTT
301   ------+---------+---------+---------+---------+---------+   360
      TGGTAGGGCCGGGGGTGCCCGGTTCTTACTCCGGGTCGTCTTTAGTCTGAACCTCGACGAA
      ThrIleProAlaProThrGlyLysAsnGluAlaGlnGlnLysSerAspLeuGluLeuLeu  -
```

FIG. 2-B

```
361 CGCATCTCACTGCTCCTCATCCAGTCGTGGCTTGGGCCCCTGCAGTTCCTCAGCAGAGTC
    ------------+---------+---------+---------+---------+---------+ 420
    GCGTAGAGTGACGAGGAGTAGGTCAGCAGCACCGAACCCGGGGACGTCAAGGAGTCGTCTCAG
    ArgIleSerLeuLeuLeuIleGlnSerTrpLeuGlyProLeuGlnPheLeuSerArgVal  -

421 TTCACCAACAGCTTGGTGTTTGGCACCTCGGACCGTGTCTATGAGAAGCTGAAGGACCTG
    ------------+---------+---------+---------+---------+---------+ 480
    AAGTGGTTGTCGAACCACAAACCGTGGAGCCTGGCACAGATACTCTTCGACTTCCTGGAC
    PheThrAsnSerLeuValPheGlyThrSerAspArgValTyrGluLysLeuLysAspLeu  -

481 GAGGAAGGCATCCTGGCCCCTGATGCGGGGAGCTGGAAGATGGCACCCCCCGGGCTGGGCAG
    ------------+---------+---------+---------+---------+---------+ 540
    CTCCTTCCGTAGGACCGGGACTACGCCCCTGACTTCTACCGTGGGGGGCCCGACCCGTC
    GluGluGlyIleLeuAlaLeuMetArgGluLeuGluAspGlyThrProArgAlaGlyGln  -

541 ATCCTCAAGCAGAGACCTATGACACAAAATTTGACAACTGTGTTGTACGGTCACTGCTGCCGGACGAG
    ------------+---------+---------+---------+---------+---------+ 600
    TAGGAGTTCGTCTGGATACTGTTTAAACTGTTGACAAATTGACAACATGCCAGTGACGACGCGGCTGCTC
    IleLeuLysGlnThrTyrAspLysPheAspThrAsnMetArgSerAspAlaLeuLeu  -
```

FIG. 2-C

```
601 AAGAACTACGGTCTGCTCTCCTGCTTCCGGAAGGACCTGCATAAGACGGAGACGTACCTG  660
        ----------+---------+---------+---------+---------+---------+
       TTCTTGATGCCAGACGAGAGGACGAAGGCCTTCCTGGACGTATTCTGCCTCTGCATGGAC
       LysAsnTyrGlyLeuLeuSerCysPheArgLysAspLeuHisLysThrGluThrTyrLeu

XbaI  HindIII
                                               —    —
661    AGGGTCATGAAGTGCCGCCGCTTCGGGGAGGCCAGTGCGCCTTCTAGAAGCTT
        ----------+---------+---------+---------+---------+
       TCCCAGTACTTCACGGGCGGCGAAGCCCCTCCGGTCGACGCGGAAGATCTTCGAA
       ArgValMetLysCysArgArgPheGlyGluAlaSerCysAlaPheEnd
```

FIG. 2-D

```
       recA  operator                    -35                                          -10
       EcoRI
       GAATTCTACTGTATGAGCATACAGTAACGCTTGACAACCGATATTTATTCACTTAATATA
    1  ----+----|----+----|----+----|----+----|----+----|----+     60
       CTTAAGATGACATACTCGTATGTCATTGCGAACTGTTGGCTATAAATAAGTGAATTATAT TAAATATCAACTGAGGCGCGCC
   61  ----+----|----+----|---
       ATTTATAGTTGACTCCGCGCGG
                       AscI
```

FIG. 4

```
       recA  operator                    -35                                          -10
       EcoRI
       GAATTCTACTGTATGAGCATACAGTAAGGGTTGACAACCGATATTTATTCACTTAATATATAA
    1  ----+----|----+----|----+----|----+----|----+----|----+----|---
       CTTAAGATGACATACTCGTATGTCATTCCCAACTGTTGGCTATAAATAAGTGAATTATATATT ATATCAACTGAGGCGCGCC
   64  ----+----|----+----
       TATAGTTGACTCCGCGCGG
                    AscI
```

FIG. 5

```
     recA                                   -10
EcoRI  operator  -35
GAATTCTCTACTGTGTATGAGCATACAGTTAAGGGTTGACAACCGATATTTATTCACTTAATAT
1  ----+---------+---------+---------+---------+---------+  60
CTTAAGAGATGACATACTCGTATGTCAATTCCCAACTGTTGGCTATAAATAAGTGAATTATA ATAAATATCAACTGAGGCGCC
61 ----+---------+----
TATTTATAGTTGACTCCGCGG
                 AscI
```

FIG. 6

```
     recA                                   -10
EcoRI  operator  -35
GAATTCTCTACTGTGTATGAGCATACAGTATAAGGGTTGACAACCGATATTTATTCACTTAATAT
1  ----+---------+---------+---------+---------+---------+-  61
CTTAAGAGATGACATACTCGTATGTCATATTCCCAACTGTTGGCTATAAATAAGTGAATTATA ATAAATATCAACTGAGGCGCC
62 ----+---------+----
TATTTATAGTTGACTCCGCGG
                 AscI
```

FIG. 7

```
              recA                    -35                                          -10
       EcoRI operator
       GAATTCTACTGTACATCCATACAGTAACGCTTGACAACCGATATTTATTCACTTAATATAA
    1  ------+---------+---------+---------+---------+---------+----
       CTTAAGATGACATGTAGGTATGTCATTGCGAACTGTTGGCTATAAATAAGTGAATTATATT ATATCAACTGAGGGCGCC
    64 ------+---------+-
       TATAGTTGACTCCCGCGG
              AscI
```

FIG. 8

```
              recA                         -35                                          -10
       EcoRI operator
       GAATTCTACTGTGTATGAGCATACAGTAAAGGGTTGACAACCGATATTTATTCACTTAATAT
    1  ------+---------+---------+---------+---------+---------+ 60
       CTTAAGATGACACTACTCGTATGTCATTTCCCAACTGTTGGCTATAAATAAGTGAATTATA ATAAATATCAACTGAGGGCGCC
    61 ------+---------+----
       TATTTATAGTTGACTCCCGCGG
                AscI
```

FIG. 9

```
         recA
         EcoRI operator                  -35                                        -10
     GAATTCTACTGTATGAGGCATACAGTAACGCTTGACACAGTCGGGGCGTGTAAGTTCTATGATA
   1 ----+----+----+----+----+----+----+----+----+----+----+----+ 60
     CTTAAGATGACATACTCGTATGTCATTGCGAACTGTGTCAGCCCGCACATTCAAGATACTAT

CACACAGGGCGCC
  61 ----+----- 74
     GTGTGTCCCGCGG
```

FIG. 10

```
         trp
         EcoRI operator                  -35                                        -10
     GAATTCTAGAACTAGTTAACTAGTACGCACGCTTGACAACCGATATTTATTCACTTAATATATAA
   1 ----+----+----+----+----+----+----+----+----+----+----+----+---- 
     CTTAAGATCTTGATCAATTGATCATGCGTGCGAACTGTTGGCTATAAATAAGTGAATTATATATT ATATCAACTGAGGGCGCC
  66 ----+----+----- 
     TATAGTTGACTCCCGCGG
            AscI
```

FIG. 11

```
              recA                  -35                            -10
       EcoRI operator
       GAATTCTACTGTATGAGCATACAGTTAAGGGTTGACAACCGATATTTATTCACTTAATAT
  1    ----+----+----+----+----+----+----+----+----+----+----+----+  60
       CTTAAGATGACATACTCGTATGTCAATTCCCAACTGTTGGCTATAAATAAGTGAATTATA AscI       ompF RBS
       ATAAATATCAACTGAGGCGCGCCAAAAAAACCATGAGGGTAATAAATAAATGTTTCCAGCA
 61    ----+----+----+----+----+----+----+----+----+----+----+----+ 120
       TATTTATAGTTGACTCCGCGCGGTTTTTTTGGTACTCCCATTATTTATTTACAAAGGTCGT
                                                          MetPheProAla BlpI
       ATGTCATTGTCCGGATTGTTTGCAAACGCCGTGCTCCGGGCTCAGC
121    ----+----+----+----+----+----+----+----+----+- 166
       TACAGTAACAGGCCTAACAAACGTTTGCGGCACGAGGCCCGAGTCG
       MetSerLeuSerGlyLeuPheAlaAsnAlaValLeuArgAlaGln
```

FIG. 12

SEQUENCE LISTING

```
<160> NUMBER OF SEQ ID NOS: 12

<210> SEQ ID NO 1
<211> LENGTH: 714
<212> TYPE: DNA
<213> ORGANISM: SYNTHETIC
<220> FEATURE:
<221> NAME/KEY: CDS
<222> LOCATION: (133)..(705)

<400> SEQUENCE: 1
gaattctact gtatgagcat acagtaacgc ttgacaaccg atatttattc acttaatata      60
taaatatcaa ctgaggcgcg cctaaaaagg gtatcgacaa tgtatcgcga tttaaataag     120
gaggaataac at atg ttc cca gcc atg tcc ttg tcc ggc ctg ttt gcc aac    171
              Met Phe Pro Ala Met Ser Leu Ser Gly Leu Phe Ala Asn
                1               5                  10 gct gtg ctc cgg gct cag cac ctg cat cag ctg gct gct gac acc ttc      219
Ala Val Leu Arg Ala Gln His Leu His Gln Leu Ala Ala Asp Thr Phe
    15                  20                  25 aaa gag ttt gag cgc acc tac atc ccg gag gga cag aga tac tcc atc      267
Lys Glu Phe Glu Arg Thr Tyr Ile Pro Glu Gly Gln Arg Tyr Ser Ile
 30                  35                  40                  45 cag aac acc cag gtt gcc ttc tgc ttc tct gaa acc atc ccg gcc ccc      315
Gln Asn Thr Gln Val Ala Phe Cys Phe Ser Glu Thr Ile Pro Ala Pro
                 50                  55                  60 acg ggc aag aat gag gcc cag cag aaa tca gac ttg gag ctg ctt cgc      363
Thr Gly Lys Asn Glu Ala Gln Gln Lys Ser Asp Leu Glu Leu Leu Arg
             65                  70                  75 atc tca ctg ctc ctc atc cag tcg tgg ctt ggg ccc ctg cag ttc ctc      411
Ile Ser Leu Leu Leu Ile Gln Ser Trp Leu Gly Pro Leu Gln Phe Leu
         80                  85                  90 agc aga gtc ttc acc aac agc ttg gtg ttt ggc acc tcg gac cgt gtc      459
Ser Arg Val Phe Thr Asn Ser Leu Val Phe Gly Thr Ser Asp Arg Val
     95                 100                 105 tat gag aag ctg aag gac ctg gag gaa ggc atc ctg gcc ctg atg cgg      507
Tyr Glu Lys Leu Lys Asp Leu Glu Glu Gly Ile Leu Ala Leu Met Arg
110                 115                 120                 125 gag ctg gaa gat ggc acc ccc cgg gct ggg cag atc ctc aag cag acc      555
Glu Leu Glu Asp Gly Thr Pro Arg Ala Gly Gln Ile Leu Lys Gln Thr
                130                 135                 140 tat gac aaa ttt gac aca aac atg cgc agt gac gac gcg ctc ctc aag      603
Tyr Asp Lys Phe Asp Thr Asn Met Arg Ser Asp Asp Ala Leu Leu Lys
```

-continued

```
                    145                 150                 155
aac tac ggt ctg ctc tcc tgc ttc cgg aag gac ctg cat aag acg gag        651
Asn Tyr Gly Leu Leu Ser Cys Phe Arg Lys Asp Leu His Lys Thr Glu
        160                 165                 170 acg tac ctg agg gtc atg aag tgc cgc cgc ttc ggg gag gcc agc tgc        699
Thr Tyr Leu Arg Val Met Lys Cys Arg Arg Phe Gly Glu Ala Ser Cys
    175                 180                 185 gcc ttc tagaagctt                                                      714
Ala Phe
190
```

<210> SEQ ID NO 2
<211> LENGTH: 191
<212> TYPE: PRT
<213> ORGANISM: SYNTHETIC

<400> SEQUENCE: 2

```
Met Phe Pro Ala Met Ser Leu Ser Gly Leu Phe Ala Asn Ala Val Leu
 1               5                  10                  15

Arg Ala Gln His Leu His Gln Leu Ala Ala Asp Thr Phe Lys Glu Phe
            20                  25                  30

Glu Arg Thr Tyr Ile Pro Glu Gly Gln Arg Tyr Ser Ile Gln Asn Thr
        35                  40                  45

Gln Val Ala Phe Cys Phe Ser Glu Thr Ile Pro Ala Pro Thr Gly Lys
    50                  55                  60

Asn Glu Ala Gln Gln Lys Ser Asp Leu Glu Leu Leu Arg Ile Ser Leu
65                  70                  75                  80

Leu Leu Ile Gln Ser Trp Leu Gly Pro Leu Gln Phe Leu Ser Arg Val
                85                  90                  95

Phe Thr Asn Ser Leu Val Phe Gly Thr Ser Asp Arg Val Tyr Glu Lys
            100                 105                 110

Leu Lys Asp Leu Glu Glu Gly Ile Leu Ala Leu Met Arg Glu Leu Glu
        115                 120                 125

Asp Gly Thr Pro Arg Ala Gly Gln Ile Leu Lys Gln Thr Tyr Asp Lys
    130                 135                 140

Phe Asp Thr Asn Met Arg Ser Asp Asp Ala Leu Leu Lys Asn Tyr Gly
145                 150                 155                 160

Leu Leu Ser Cys Phe Arg Lys Asp Leu His Lys Thr Glu Thr Tyr Leu
                165                 170                 175

Arg Val Met Lys Cys Arg Arg Phe Gly Glu Ala Ser Cys Ala Phe
            180                 185                 190
```

<210> SEQ ID NO 3
<211> LENGTH: 82
<212> TYPE: DNA
<213> ORGANISM: SYNTHETIC

<400> SEQUENCE: 3
gaattctact gtatgagcat acagtaacgc ttgacaaccg atatttattc acttaatata        60
taaatatcaa ctgaggcgcg cc                                                 82

<210> SEQ ID NO 4
<211> LENGTH: 82
<212> TYPE: DNA
<213> ORGANISM: SYNTHETIC

<400> SEQUENCE: 4
gaattctact gtatgagcat acagtaaggg ttgacaaccg atatttattc acttaatata        60

-continued

```
taaatatcaa ctgaggcgcg cc                                            82

<210> SEQ ID NO 5
<211> LENGTH: 83
<212> TYPE: DNA
<213> ORGANISM: SYNTHETIC

<400> SEQUENCE: 5
gaattctact gtatgagcat acagttaagg gttgacaacc gatatttatt cacttaatat   60
ataaatatca actgaggcgc gcc                                           83

<210> SEQ ID NO 6
<211> LENGTH: 84
<212> TYPE: DNA
<213> ORGANISM: SYNTHETIC

<400> SEQUENCE: 6
gaattctact gtatgagcat acagtataag ggttgacaac cgatatttat tcacttaata   60
tataaatatc aactgaggcg cgcc                                          84

<210> SEQ ID NO 7
<211> LENGTH: 82
<212> TYPE: DNA
<213> ORGANISM: SYNTHETIC

<400> SEQUENCE: 7
gaattctact gtacatccat acagtaacgc ttgacaaccg atatttattc acttaatata   60
taaatatcaa ctgaggcgcg cc                                            82

<210> SEQ ID NO 8
<211> LENGTH: 83
<212> TYPE: DNA
<213> ORGANISM: SYNTHETIC

<400> SEQUENCE: 8
gaattctact gtatgagcat acagtaaagg gttgacaacc gatatttatt cacttaatat   60
ataaatatca actgaggcgc gcc                                           83

<210> SEQ ID NO 9
<211> LENGTH: 74
<212> TYPE: DNA
<213> ORGANISM: SYNTHETIC

<400> SEQUENCE: 9
gaattctact gtatgagcat acagtaacgc ttgacagtcg ggcgtgtaag ttctatgata   60
cacacaggcg cgcc                                                     74

<210> SEQ ID NO 10
<211> LENGTH: 84
<212> TYPE: DNA
<213> ORGANISM: SYNTHETIC

<400> SEQUENCE: 10
gaattctaga actagttaac tagtacgcac gcttgacaac cgatatttat tcacttaata   60
tataaatatc aactgaggcg cgcc                                          84

<210> SEQ ID NO 11
<211> LENGTH: 166
<212> TYPE: DNA
```

-continued

```
<213> ORGANISM: SYNTHETIC
<220> FEATURE:
<221> NAME/KEY: CDS
<222> LOCATION: (109)..(165)

<400> SEQUENCE: 11
gaattctact gtatgagcat acagttaagg gttgacaacc gatatttatt cacttaatat      60
ataaatatca actgaggcgc gccaaaaaaa ccatgagggt aataaata atg ttt cca      117
                                                    Met Phe Pro
                                                      1
gca atg tca ttg tcc gga ttg ttt gca aac gcc gtg ctc cgg gct cag c    166
Ala Met Ser Leu Ser Gly Leu Phe Ala Asn Ala Val Leu Arg Ala Gln
      5                  10                 15

<210> SEQ ID NO 12
<211> LENGTH: 19
<212> TYPE: PRT
<213> ORGANISM: SYNTHETIC

<400> SEQUENCE: 12

Met Phe Pro Ala Met Ser Leu Ser Gly Leu Phe Ala Asn Ala Val Leu
  1               5                  10                 15

Arg Ala Gln
```

DNA CONSTRUCT FOR REGULATING THE EXPRESSION OF A POLYPEPTIDE CODING SEQUENCE IN A TRANSFORMED BACTERIAL HOST CELL

This application claims the benefit of provisional application Ser. No. 60/127,449, filed Apr. 1, 1999.

This invention relates to materials and methods for expressing a heterologous polypeptide in a bacterial host. The heterologous polypeptide is expressed under the control of a DNA construct containing a promoter region which is derived from a cyanophage or cyanobacteria promoter. In an embodiment of the invention, such a promoter region is operably linked to an operator region which is derived from an operator native to the host cell. In another embodiment, such a promoter region is operably linked to an operator that is positioned upstream of the promoter region.

BACKGROUND OF THE INVENTION

Recombinant DNA techniques have resulted in the production of heterologous polypeptides in bacterial hosts. However, the efficiency, regulation and polypeptide yield in such systems can vary depending on factors including the nature of the host bacteria, the type of heterologous polypeptide and the DNA fragments operably linked to the polypeptide coding sequence that control its expression.

One expression control element is the promoter, alternately referred to as a promoter region, which is a segment of DNA containing the site where RNA polymerase specifically binds and initiates RNA synthesis, or transcription, of the polypeptide coding sequence. The site on the promoter generally associated with RNA polymerase binding is referred to as the $-35$ consensus sequence and the promoter site generally associated with initiation of RNA synthesis by separation of the double stranded DNA into single stranded DNA for transcription is referred to as the $-10$ consensus sequence. Various promoters have been studied and used to express genes in bacterial hosts, including promoters that are not native to the bacterial host. For example, the trp and lac promoters have been isolated from E. coli and inserted into expression cassettes used to transform non-E. coli bacteria and express heterologous proteins. In order for transcription to take place, however, these non-native promoters must be recognized by the RNA polymerase of the host bacteria.

Not only must the expression system be recognized by the host cell, but the timing of the expression may need to be regulated to ensure that the heterologous protein production occurs at a suitable time, e.g., after sufficient growth and replication of host cells, at a suitable rate and for a sufficient period of time. For example, in a large scale fermentation, it may be desirable to control the production level of heterologous protein to prevent lethal overproduction in the host cell or interference with other cell functions, as well as to ensure optimal culture conditions and polypeptide recovery.

One naturally-occurring way for some bacteria to further control expression is by use of an operator element to regulate transcription. The operator is a segment of DNA operably connected to the promoter and acts as a binding site for a repressor protein or an activator protein. When a repressor protein binds to an operator, transcription from a promoter is shut off. Conversely, binding of an activator protein to an operator turns on transcription from a promoter. For both repressed and activated systems, transcription can be turned on by a process termed induction, in which the repressor protein is inactivated or in which the activator protein is activated. The net result of both types of induction is that RNA polymerase is able to bind to the promoter and initiate transcription. An expression control system involving a promoter/operator combination should be readily turned on and off and not be "leaky", that is, producing a significant level of polypeptide either when the repressor protein is bound to an operator or when the activator protein is not bound to an operator.

Synthetic expression control systems have also been constructed that combine control elements from different sources. For example, Henner et al., U.S. Pat. No. 4,912,046, reports two hybrid promoter/operator constructs: (i) the pac-1 hybrid promoter/operator having its promoter RNA polymerase recognition site from the penicillinase promoter and an operator region from the lac promoter/operator and (ii) the spac-1 hybrid promoter/operator having its promoter RNA polymerase recognition site from a SPO-1 phage promoter and an operator from the lac promoter/operator. Henner et al. reports that the pac-1 hybrid promoter/operator was used to express B. licheniformis penicillinase in Bacillus subtilis and that the spac-1 hybrid promoter/operator was used to express leukocyte interferon in Bacillus subtilis. Additional hybrid promoter/operator systems are described by DeBoer, U.S. Pat. No. 4,551,433, which describes hybrid constructs having portions taken from the lac, trp and rrn promoter/operators. In these constructs, the promoter element is actually a hybrid promoter having its $-10$ consensus sequence contributed from one source and its $-35$ consensus sequence contributed from a different source.

Nonetheless, there is a need in the art for greater availability of expression control regions to regulate the expression of heterologous polypeptides in bacterial hosts, preferably exhibiting good expression control with high polypeptide yield.

SUMMARY OF THE INVENTION

This invention relates to materials and methods for expressing a heterologous polypeptide coding sequence in a bacterial host. The heterologous polypeptide is expressed under the control of a DNA construct containing a heterologous promoter region which is derived from a cyanophage or cyanobacteria promoter and which is operably linked to the coding sequence for the polypeptide. In one embodiment of the invention, such a promoter region is operably linked to an operator region that is derived from an operator native to the host cell. In another embodiment, the promoter region is operably linked to an operator region which is located upstream of the promoter region. In a specific embodiment, the invention utilizes a DNA construct for regulating expression of a heterologous polypeptide coding sequence in a transformed bacterial host cell, said DNA construct comprising (a) a promoter region derived from a cyanophage promoter, wherein the promoter region contains a $-10$ consensus sequence and a $-35$ consensus sequence, operably linked to (b) an operator region which is derived from an operator native to the host cell and which is located upstream of the promoter region. Each of these DNA constructs can be integrated into an expression vector which can be used to transform a bacterial host and enable production of the heterologous polypeptide.

The invention also encompasses methods of producing a heterologous polypeptide in a transformed bacterial host, comprising (a) stably transforming a bacterial host with a vector containing a heterologous polypeptide coding sequence operably linked to any of the above-mentioned DNA constructs for regulating expression of the coding sequence and (b) culturing the transformed bacteria under conditions that induce expression of the coding sequence.

The invention is also directed to expression vectors, transformed bacteria, and bacterial cultures containing such DNA constructs.

DESCRIPTION OF THE FIGURES

Figure 2:
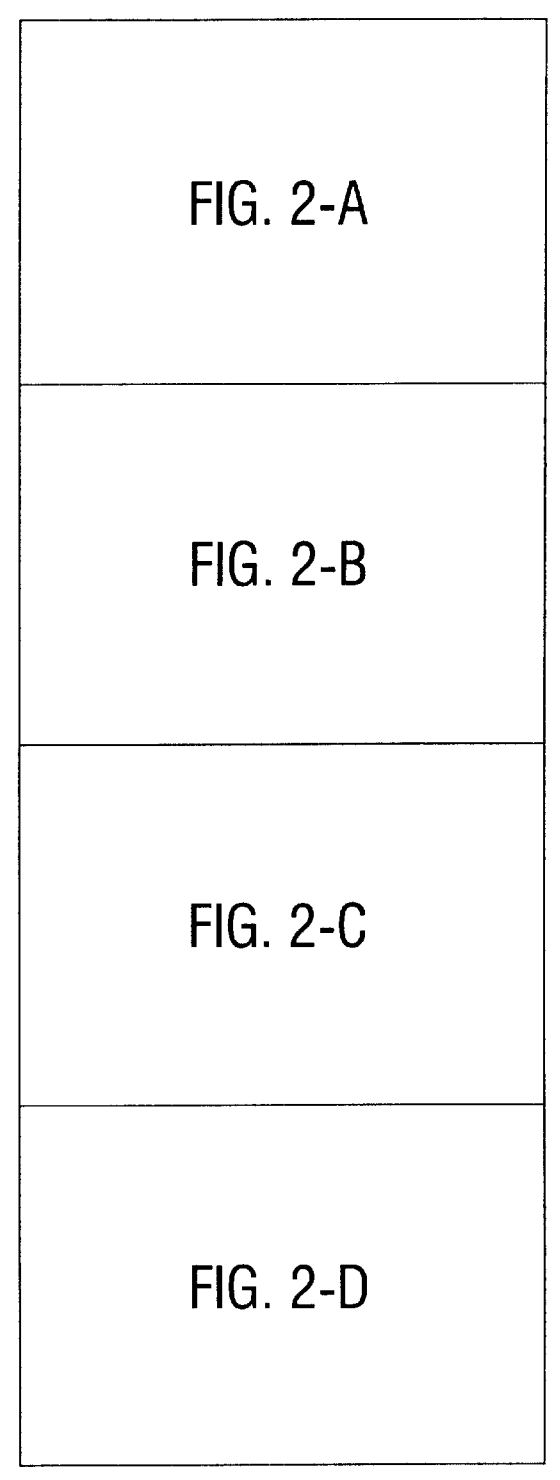

FIGS. 2A–2D show a DNA sequence (SEQ ID NO: 1) of the EcoRI/HindIII fragment of a) pCPEX-9, which contains a promoter/operator construct according to the invention, a two cistron ribosome binding site, and a bovine somatotropin (bST) gene.

FIG. 4 is a DNA sequence (SEQ ID NO:3) of an inventive promoter/operator construct containing an operator region derived from the recA operator and a promoter region derived from the cyanophage N-1 early gene promoter.

FIG. 5 is a DNA sequence (SEQ ID NO:4) of an inventive promoter/operator construct containing an operator region derived from the recA operator and a promoter region derived from the cyanophage N-1 early gene promoter.

FIG. 6 is a DNA sequence (SEQ ID NO:5) of an inventive promoter/operator construct containing an operator region derived from the recA operator and a promoter region derived from the cyanophage N-1 early gene promoter.

FIG. 7 is a DNA sequence (SEQ ID NO:6) of an inventive promoter/operator construct containing an operator region derived from the recA operator and a promoter region derived from the cyanophage N-1 early gene promoter.

FIG. 8 is a DNA sequence (SEQ ID NO:7) of an inventive promoter/operator construct containing an operator region derived from the recA operator and a promoter region derived from the cyanophage N-1 early gene promoter.

FIG. 9 is a DNA sequence (SEQ ID NO:8) of an inventive promoter/operator construct containing an operator region derived from the recA operator and a promoter region derived from the cyanophage N-1 early gene promoter.

FIG. 10 is a DNA sequence (SEQ ID NO:9) of an inventive promoter/operator construct containing an operator region derived from the recA operator and a promoter region derived from the *Rhodobacter capsulatus* promoter.

FIG. 11 is a DNA sequence (SEQ ID NO:10) of an inventive promoter/operator construct containing an operator region derived from the trp operator and a promoter region derived from the cyanophage N-1 early gene promoter.

FIG. 12 is a DNA sequence (SEQ ID NO:11) of an inventive promoter/operator construct containing an operator region derived from and the recA operator and the single cistron ompF ribosome binding site and a promoter region derived from the cyanophage N-1 early gene promoter.

DESCRIPTION OF ILLUSTRATIVE EMBODIMENTS

Figure 1:
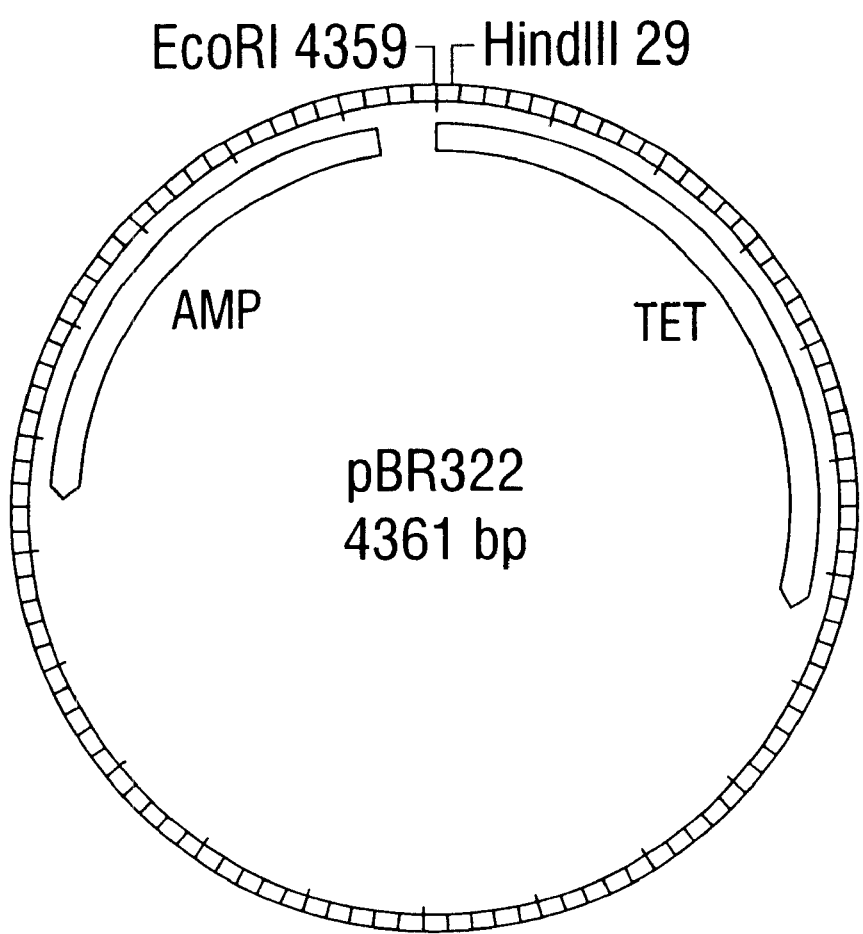
FIG. 1 is a plasmid map for cloning vector pBR322, which carries genes for ampicillin and tetracycline resistance.

This invention relates to materials and methods for expressing heterologous polypeptides in bacterial hosts. More particularly, the invention involves a DNA construct for regulating the expression of a polypeptide coding sequence in a transformed bacterial host cell, wherein the construct contains a heterologous promoter region which is derived from a cyanophage or cyanobacteria promoter and is operably linked to the polypeptide coding sequence. Optionally, such a promoter region is operably linked to an operator region derived from an operator native to the host cell. Also optionally, such a promoter region is operably linked an operator region that is positioned upstream of the promoter region.

For purposes of the present invention, the term "derived from," in the context of the promoter and operator regions of the inventive expression control construct, means that the DNA sequence corresponds to, or is based on a naturally-occurring sequence or a naturally-occurring sequence, optionally with modifications, i.e., one or more nucleotide substitutions, additions or deletions that do not reduce, to an unacceptable degree, the ability of the expression control construct to regulate expression of the heterologous polypeptide. For example the construct of SEQ ID NO. 10 (also depicted in FIG. 11) contains an operator region derived from the trp operator, which is native to *E. coli*. The operator region of SEQ ID NO. 10 differs from the naturally-occurring trp operator in that it has a one nucleotide substitution. Similarly, the promoter region of the invention may be based on either a naturally occurring sequence or a naturally occurring sequence with modifications that do not substantially reduce the rate of transcription or the level of transcription control.

Conventional methods have been developed for the construction of transformation and expression vectors, the insertion of coding sequences for polypeptides of interest into those vectors, and the introduction of the resulting vectors into bacterial hosts. Such methods are described, for example in publications including Bernard et al. (1979); Wu (1979); Grossman and Moldave (1980); Remaut et al. (1981); Perbal (1988); and Maniatis et al. (1989).

The bacterial host is generally any bacteria in which the inventive promoter/operator construct can function to control expression of a heterologous polypeptide coding sequence. More particularly, the host bacteria should have the ability to make a repressor protein, either naturally or via genetic engineering, that is capable of binding to the operator of the inventive promoter/operator construct. The RNA polymerase of the bacterial host, produced naturally or via genetic engineering, should also have the ability to bind to the promoter for initiation of transcription. Preferably, the bacterial host is one that naturally produces a repressor protein capable of regulating expression of the heterologous polypeptide by binding to the operator of the inventive promoter/operator construct. For example, certain bacteria from the Enterobacteriacea, such as *E. coli* and *Salmonella typhimurium*, and *Rhodobacter capsulatus* have the ability to produce such a repressor protein.

In a preferred embodiment, the promoter region is derived from cyanobacteria or cyanophage, and more particularly from cyanophage N-1. Cyanobacteria (also called blue-green algae) are considered very distant to other bacteria because they have a photosynthesis system similar to that of higher plants, can use light as an energy source, biosynthesize organic substances from water and carbon dioxide and slight amounts of inorganic salts, and autotrophically proliferate. Therefore, it is also a surprising aspect of the invention that the promoter derived from cyanophage proved to be suitable for expression of a heterologous polypeptide in a bacterium such as *E. coli*.

The heterologous polypeptide to be produced may be any desired polypeptide that can be efficiently produced under the control of the inventive promoter/operator, including growth hormones, e.g., bovine, porcine or human growth hormones, granulocyte colony stimulating factor (GCSF), erythropoietin (EPO), insulin, interleukins, interferons and tissue plasminogen activator (t-PA).

The transformed host cells are grown under conditions suitable to permit production of the desired polypeptide and the resulting polypeptide is recovered.

In a preferred embodiment, the inventive control region regulates production of the heterologous polypeptide such that polypeptide expression is suppressed before induction and polypeptide expression occurs after induction. More particularly, polypeptide production should not occur to a significant degree before induction, but the polypeptide coding sequence should be highly expressed after induction. The presence of polypeptide expression can be visually observed, for example, as in the case of bST expression by the accumulation of inclusion bodies. Alternatively, the level of polypeptide expression can be measured, with preferred levels of post-induction polypeptide production being greater than 0.1 micrograms per milliliter per $OD_{550}$ unit, more preferably 0.5 micrograms per milliliter per $OD_{550}$ unit, and most preferably 1 microgram per milliliter per $OD_{550}$ unit. Where the polypeptide is bovine growth hormone, the level of expression is preferably at a level of at least 1 microgram per milliliter per $OD_{550}$ unit, more preferably 5 micrograms per milliliter per $OD_{550}$ unit, and most preferably 50 micrograms per milliliter per $OD_{550}$ unit.

In a further preferred embodiment, the DNA regulatory construct according to the invention is an expression control region having the following nucleotide sequence (SEQ ID NO:3, nucleotides 7–74):

spacer segment of approximately 4–6 nucleotides. The spacer segment may be, for example, ACGC, AGGG, TAAGGG, or AAGGG.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Construction of the Cloning Vector Used for Subsequent Plasmid Constructions

The cloning vector pBR322 (Bolivar, et al.), obtained from Boehringer Mannheim (Indianapolis, Ind.), carrying genes for ampicillin and tetracycline resistance (FIG. 1), was used in expression vector construction. Double stranded DNA fragments containing a synthetic promoter/operator (SEQ. ID NO. 3; FIG. 4), a two-cistron ribosome binding site and the bST gene flanked by restriction endonuclease recognition sites were designed, as shown in SEQ. ID NO. 1. A DNA fragment according to the inventive design was constructed by Midland Certified Reagents (Midland, Tex.) and ligated into pBR322 using standard cloning techniques (Rodriguez and Tait). This plasmid, designated pCPEX-9

```
TACTGTATGAGCATACAGTAACGCTTGACAACCGATATTTATTCACTTAATATATAAATATCAACTGA
1........10........20........30........40........50........60......68
```

Segments within this sequence are derived from different sources:

| Segment | Source |
|---|---|
| 1–20 | E. coli recA operator |
| 21–24 | Synthetic spacer |
| 25–68 | Early gene promoter region from cyanophage N-1, | including a −35 region having the sequence TTGACA (nucleotides 25–30), a −10 region having the sequence TAATAT (nucleotides 48–53) and a transcription initiation site (nucleotide 60)

The E. coli recA operator segment (nucleotides 1–20) is found in the naturally occurring recA gene at nucleotide positions −30 through −11, relative to the recA transcription initiation site (+1). In the inventive construct, the E. coli recA operator segment is positioned upstream of the cyanophage promoter segment. The construct is used in conjunction with an E. coli lexA gene encoding the LexA repressor protein, which is capable of binding to the E. coli recA operator segment.

The segment of the cyanophage N-1 early gene promoter (nucleotides 25–68) is found in the naturally occurring cyanophage at positions −35 through +9, relative to its transcription initiation site (+1).

Figure 3:
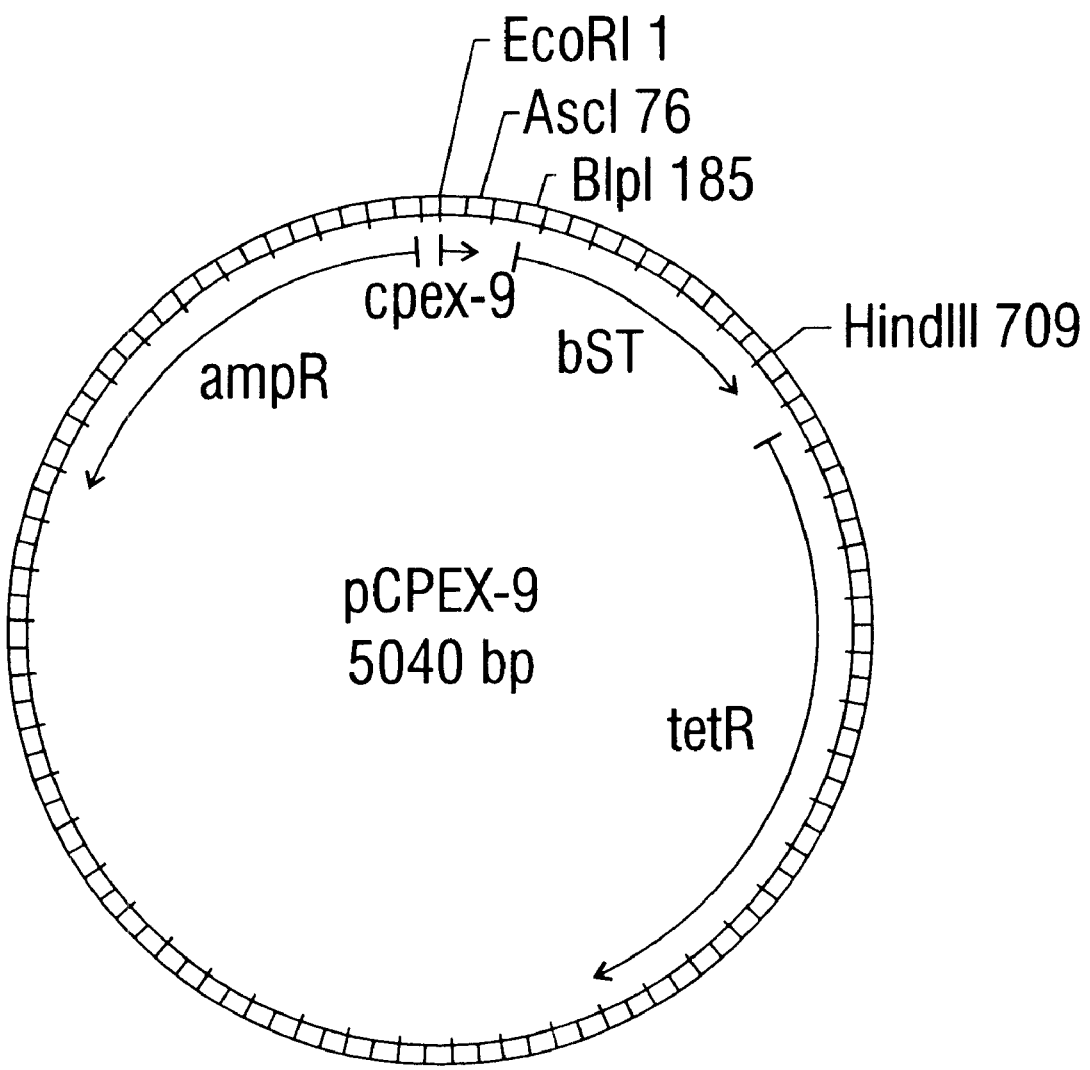
FIG. 3 is a plasmid map for pCPEX-9, which contains a synthetic DNA fragment inserted into pBR322 between the EcoRI and HindIII restriction endonuclease recognition sites. The synthetic DNA fragment contains a promoter/operator construct according to the invention, a ribosome binding site, and a bST gene.

Between the E. coli recA operator segment and the cyanophage N-1 early gene promoter segment is a short (FIG. 3), contains the synthetic DNA fragments replacing the small EcoRI-HindIII fragment of the pBR322 vector.

Example 2

Construction of bST Expression Vectors Having a Promoter Element Derived From a Cyanophage N-1 Early Gene Promoter and an Operator Derived From the E. coli recA Operator Following construction of pCPEX-9, the EcoRI and AscI sites were used for cloning of alternate promoter/operator fragments. The promoter/operators were designed as EcoRI/AscI fragments containing an operator derived from the E. coli recA promoter (an "SOS box"; Friedberg, et al., 1985; this operator will be referred to as the "recA operator") located upstream of the cyanophage N-1 early gene promoter (Schneider and Haselkorn). The linker region between the operator and −35 promoter region is between 4 and 6 base pairs. Minor variations in the operator region are permissible. These fragments according to the inventive design were also constructed by Midland Certified Reagents. Examples are shown in SEQ. ID NOS. 4–8 (also depicted in FIGS. 5–9).

Two and a half micrograms of pCPEX-9 were digested with 10 units each of the restriction endonucleases EcoRI and AscI in buffer containing 50 mM potassium acetate, 20 mM Tris-acetate, 10 mM magnesium acetate, 1 mM dithiothreitol (pH 7.9). These mixtures were incubated at 37° C. for 1 hour.

The restriction endonucleases were removed from the digestion reactions with a Wizard DNA Clean-up Kit (Promega, Madison, Wis.) following the manufacturer's instructions, and the DNA eluted with 30 µl of sterile water. The ligation reaction was prepared as follows and incubated at 15° C. overnight:

| | |
|---|---|
| 10 µl | EcoRI and AscI digested pCPEX-9 |
| 1 µl | Synthetic DNA fragment (resuspended to a final concentration of 0.25 µg/ml in sterile water) |
| 5 µl | sterile water |
| 5 units | T4 DNA ligase (Boehringer Mannheim, Indianapolis, IN) |
| 1.6 µl | T4 DNA ligase buffer (Boehringer Mannheim, Indianapolis, IN) |

66 mM Tris-HCl, 5 mM MgCl2, 1 mM dithioerythritol, 1 mM ATP, pH 7.5.

The ligated DNA was transformed directly into competent E. coli DH5α cells (Gibco BRL, Bethesda Md.) according to the manufacturer's instructions (Hanahan, 1983). Transformed cells were selected by plating the transformation mixture on Luria broth agar plates containing 100 µg/ml ampicillin and incubating the plates at 37° C. for 24 hours. All media components were obtained from Difco Laboratories (Detroit, Mich.). Ampicillin was obtained from Sigma Chemicals (St. Louis, Mo.).

Individual clones were sequenced with the primer EKBGH. This primer yielded nucleotide sequences covering the entire EcoRI/AscI insert, allowing confirmation of integration of the desired synthetic fragment. Sequencing was performed using ABI automated sequencing and Perkin-Elmer reagents (Perkin-Elmer Corp., Foster City, Calif.).

Plasmids were transformed into E. coli W3110 cells using standard procedures (Seidman, et al.). Transformed cells were selected by plating the transformation mixture on Luria broth agar plates containing 100 µg/ml ampicillin and incubating the plates at 37° C. for 24 hours.

Example 3

Construction of a bST Expression Vector Having a Promoter Element Derived From *Rhodobacter Capsulatus* and an Operator Derived From recA Operator A DNA fragment (SEQ. ID NO. 9; FIG. 10) containing a synthetic promoter/operator including the *Rhodobacter capsulatus* bchCXYZ promoter (Ma, D., et al., 1993) and the recA operator located upstream of the −35 promoter region according to the inventive design was as constructed by Midland Certified Reagents and resuspended to a final concentration of 0.25 µg/µl in sterile water.

Two and a half micrograms of pCPEX-9 were digested with 10 units each of the restriction endonuclease EcoRI and AscI in buffer containing 50 mM potassium acetate, 20 mM Tris-acetate, 10 mM magnesium acetate, 1 mM dithiothreitol (pH 7.9). These mixtures were incubated at 37° C. for 1 hour.

The restriction endonucleases were removed from the digestion reactions with Wizard DNA Clean-up Kit following the manufacturer's instructions and the DNA eluted with 30 µl of sterile water. The ligation reaction was prepared as follows and incubated at 15° C. overnight.

| | |
|---|---|
| 10 µl | EcoRI and AscI digested pCPEX-9 |
| 1 µl | Synthetic DNA fragment |
| 5 µl | sterile water |
| 5 units | T4 DNA ligase |
| 1.6 µl | T4 DNA ligase buffer |

The ligated DNA was transformed directly into competent E. coli DH5α according to the Hanahan (1983). Transformed cells were selected by plating the transformation mixture on Luria broth agar plates containing 100 µg/ml ampicillin and incubating the plates at 37° C. for 24 hours.

Individual clones were sequenced with the primer EKBGH. This primer yielded nucleotide sequence covering the entire EcoRI/AscI insert, allowing confirmation of integration of the desired synthetic fragment. Sequencing was performed using ABI automated sequencing and Perkin-Elmer. The newly constructed plasmid was transformed into E. coli W3110 using standard procedures and transformants were selected by plating the transformation mixture on Luria broth agar plates containing 100 µg/ml ampicillin and incubating the plates at 37° C. for 24 hours.

Example 4

Construction of a bST Expression Vector Having a Promoter Element Derived From Cyanophage N-1 and the E. coli trp Operator A DNA fragment SEQ. ID NO. 10 (also depicted in FIG. 11) containing a synthetic promoter/operator including the cyanophage N-1 early gene promoter and an operator derived from the E. coli trp promoter (Platt, 1978, hereinafter referred to as the "trp operator") positioned upstream of the −35 promoter region according to the inventive design was constructed by Midland Certified Reagents and resuspended to a final concentration of 0.25 µg/µl in sterile water.

Two and a half micrograms of pCPEX-9 were digested with 10 units each of the restriction endonucleases EcoRI and AscI in buffer containing 50 mM potassium acetate, 20 mM Tris-acetate, 10 mM magnesium acetate, 1 mM dithiothreitol (pH 7.9). These mixtures were incubated at 37° C. for 1 hour.

The restriction endonucleases were removed from the digestion reactions with Wizard DNA Clean-up Kit following the manufacturer's instructions and the DNA eluted with 30 µl of sterile water. The ligation reaction was prepared as follows and incubated at 15° C. overnight;

| | |
|---|---|
| 10 µl | EcoRI/AscI digested pCPEX-9 |
| 1 µl | Synthetic DNA fragment |
| 5 µl | sterile water |
| 5 units | T4 DNA ligase |
| 1.6 µl | T4 DNA ligase buffer |

The ligated DNA was transformed directly into competent E. coli DH5α according to Hanahan (1983). Transformed cells were selected by plating the transformation mixture on Luria broth agar plates containing 100 µg/ml ampicillin and incubating the plates at 37° C. for 24 hours.

Individual clones were sequenced with the primer EKBGH. This primer yielded nucleotide sequence covering the entire EcoRI/AscI insert, allowing confirmation of integration of the desired synthetic fragment. Sequencing was performed using ABI automated sequencing and Perkin-Elmer reagents. The newly constructed plasmid was transformed into *E. coli* W3110 using standard procedures (Seidman et al. (1997)) and transformants were selected by plating the transformation mixture on Luria broth agar plates containing 100 μg/ml ampicillin and incubating the plates at 37° C. for 24 hours.

Example 5

Construction of bST Expression Vectors Having a Promoter Element Derived From a Cyanophage N-1 Early Gene Promoter, an Operator Derived From the *E. coli* recA Operator and the Single Cistron ompF Ribosome Binding Site Following construction of pCPEX-9, the EcoRI and BlpI sites were used for cloning of an alternate promoter/operator fragment, ribosome binding site and modified bST gene. A synthetic EcoRI/BlpI fragment was constructed containing the promoter/operator from FIG. 6 linked to the ompF ribosome binding site and the beginning of the bST gene. This fragment according to the inventive design was also constructed by Midland Certified Reagents. The sequence information is provided in SEQ. ID NO. 11 (also depicted in FIG. 12).

Two and a half micrograms of pCPEX-9 were digested with 10 units each of the restriction endonucleases EcoRI and BlpI in buffer containing 50 mM potassium acetate, 20 mM Tris-acetate, 10 mM magnesium acetate, 1 mM dithiothreitol (pH 7.9). These mixtures were incubated at 37° C. for 1 hour.

The restriction endonucleases were removed from the digestion reactions with a Wizard DNA Clean-up Kit (Promega, Madison, Wis.) following the manufacturer's instructions, and the DNA eluted with 30 μl of sterile water. The ligation reaction was prepared as follows and incubated at 15° C. overnight:

| | |
|---|---|
| 10 μl | EcoRI and BlpI digested pCPEX-9 |
| 1 μl | Synthetic DNA fragment (resuspended to a final concentration of 0.25 μg/ml in sterile water) |
| 5 μl | sterile water |
| 5 units | T4 DNA ligase (Boehringer Mannheim, Indianapolis, IN) |
| 1.6 μl | T4 DNA ligase buffer (Boehringer Mannheim, Indianapolis, IN) |

66 mM Tris-HCl, 5 mM MgCl2, 1 mM dithioerythritol, 1 mM ATP, pH 7.5

The ligated DNA was transformed directly into competent *E. coli* DH5α according to Hanahan (1983). Transformed cells were selected by plating the transformation mixture on Luria broth agar plates containing 100 μg/ml ampicillin and incubating the plates at 37° C. for 24 hours.

Individual clones were sequenced with the primer EKBGH. This primer yielded nucleotide sequence covering the entire EcoRI/BlpI insert, allowing confirmation of integration of the desired synthetic fragment. Sequencing was performed using ABI automated sequencing and Perkin-Elmer reagents. The newly constructed plasmid was transformed into *E. coli* W3110 using standard procedures and transformants were selected by plating the transformation mixture on Luria broth agar plates containing 100 μg/ml ampicillin and incubating the plates at 37° C. for 24 hours.

Example 6

Analysis of bST Expression From Plasmid Vectors Containing the Synthetic Promoter/Operator Construct Expression of bST by the synthetic promoter/bST plasmids was screened by induction of bST expression. Vogel-Bonner media (Vogel and Bonner, 1958) was inoculated with W3110 cultures containing individual expression plasmids to an initial $OD_{550}$ of 0.3 and incubated at 37° C., 300 rpm. When the $OD_{550}$ reached 0.8, the cultures were induced. Constructs containing recA operators were induced with nalidixic acid to a final concentration of 50 μg/ml. Constructs containing the trp operator were induced with indole acrylic acid to a final concentration of 25 μg/ml. Nalidixic acid and indole acrylic acid were obtained from Sigma Chemical Company, St. Louis, Mo. Cultures were grown at 37° C., 300 rpm for an additional 4 hours.

Whole cell protein samples were prepared and visualized after sodium dodecyl sulfate-polyacrylamide gel electrophoresis and staining with Coomassie blue (Laemmli, 1970). The protein gels were run with molecular weight markers (Gibco BRL, Rockville, Md.) to help pinpoint the location of the protein band corresponding to the 22,000 kilodalton bST protein. Constructs that exhibited significant bST expression before induction were considered to be due to synthetic promoters which were not regulated well enough to be useful, and constructs which exhibited insignificant bST expression after induction were considered to be due to synthetic promoters which were too weak to be useful. Those constructs that exhibited little or no bST expression prior to induction, and significant bST expression by four hours after induction, were considered to be both well-regulated and strong enough to be useful.

Those constructs that passed this initial screening were tested further in order to more precisely quantitate their bST expression levels. The strains were grown and induced in a ten liter fermentation vessel, and the bST expression levels determined by a reversed-phase high pressure liquid chromatography assay (Bogosian et al., 1989). Those constructs which expressed bST at levels greater than 5 micrograms per milliliter per $OD_{550}$ unit (constructs regulated by SEQ. ID No. 3–10) were considered particularly beneficial for the expression of heterologous proteins.

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

Bibliography

Bernard, H. U., E. Remaut, M. V. Hershfield, H. K. Das, D. R. Helinski, C. Yanofsky, and N. Franklin. 1979. Construction of plasmid cloning vehicles that promote gene expression from the bacteriophage lambda pL promoter. Gene. 5:59–76.

Bogosian, G., B. N. Violand, E. J. Dorward-King, W. E. Workman, P. E. Juing, and J. F. Kane. 1989. Biosynthesis and incorporation into protein of norleucine by *Escherichia coli*. Journal of Biological Chemistry. 264:531–539.

Bolivar, F., R. L. Rodriguez, P. J. Greene, M. C. Betlach, H. L. Heynecker and H. W. Boyer. 1977. Construction of useful cloning vectors. Gene. 2:95–113.

Friedberg, E. C., G. C. Walker, and W. Siede. 1995. DNA Repair and Mutagenesis, p. 407–464. American Society for Microbiology Press, Washington, D.C.

Grossman, L. and K. Moldave (eds.). 1980. Nucleic Acids, Part 1. Methods in Enzymology, Vol. 65.

Hanahan, D. 1983. Studies on transformation of *Escherichia coli* with plasmids. Journal of Molecular Biology. 166:557–580.

Laemmli, U. K. 1970. Cleavage of structural proteins during the assembly of the head of bacteriophage. Nature 277:680–685.

Ma, D., D. N. Cook, D. A. O'Brien, and J. E. Hearst. 1993. Analysis of the promoter and regulatory sequences of an oxygen-regulated bch operon in *Rhodobacter capsulatus* by site-directed mutagenesis. Journal of Bacteriology 175:2037–2045.

Maniatis, T., J. Sambrock and E. F. Fritsch. 1989. Molecular Cloning; A Laboratory Manual. Cold Spring Harbor Laboratory, New York.

Perbal, B. 1988. A Practical Guide to Molecular Cloning, Second Edition. Wiley Interscience, New York, N.Y.

Platt, T. 1978. Regulation of gene expression in the tryptophan operon of *Escherichia coli*, p. 263–302. In J. H. Miller and W. S. Reznikoff (ed.), The Operon. Cold Spring Harbor Laboratory, Cold Spring Harbor, N.Y.

Remaut, E. P. Stanssens and W. Fiers. 1981. Plasmid vectors for high-efficiency expression controlled by the pL promoter of coliphage lambda. Gene. 15:81–93.

Rodriguiz, R. L. and R. C. Tait. 1983. Ligation of DNA, pg. 81–98. In Recombinant DNA Techniques. Addison-Wesley Publishing Company. Reading, Mass.

Schneider, G. J. and R. Haselkorn. 1988. Characterization of two early promoters of cyanophage N-1. Virology 167:150–155.

Seidman, C. E., K. Struhl, H. Sheen and T. Jessen. 1997. One-step preparation and transformation of competent cells. p. 1.8.3. In Current Protocols in Molecular Biology. John Wiley and Sons, New York, N.Y.

Vógel, H. J. and D. M. Bonner. 1956. Acetylornithinase of *Escherichia coli*: partial purification and some properties. Journal of Biological Chemistry. 218: 97–106.

Wu, R. (ed.). 1979. Recombinant DNA. Methods in Enzymology, Vol. 68.

---

What is claimed is:

1. A DNA construct for regulating the expression of a heterologous polypeptide coding sequence in a transformed bacterial host cell, comprising:
    (a) a heterologous cyanophage N-1 early gene promoter, operably linked to
    (b) an operator segment from an operator native to the host cell, wherein the operator segment is located upstream of the promoter region.

2. A DNA construct of claim 1, wherein the polypeptide is bovine somatotropin.

3. The DNA construct of claim 1, wherein the host cell is *Escherichia coli*.

4. The DNA construct of claim 3, wherein the operator segment is from an *Escherichia coli* recA or trp operator.

5. The DNA construct of claim 1, wherein the promoter and the operator segment are connected by a spacer region.

6. The DNA construct of claim 5, wherein the spacer region is ACGC, AGGG, TAAGGG, or AAGGG.

7. A DNA construct for regulating the expression of a heterologous polypeptide coding sequence in a transformed bacterial host cell, comprising
    a heterologous promoter, operably linked to an operator segment from an operator native to the host cell, wherein the operator segment is positioned upstream of the promoter;
    wherein said operator is capable of binding to a repressor protein made by the host cell; and,
    wherein the promoter is capable of binding to an RNA polymerase produced by the bacterial host to initiate transcription, and
    wherein the promoter is a cyanophage N-1 early gene or *Rhodobacter capsulatus* promoter.

8. A DNA construct of claim 7, wherein the polypeptide is bovine somatotropin.

9. The DNA construct of claim 7, wherein the promoter and the operator segment are connected by a spacer region.

10. The DNA construct of claim 9, wherein the spacer region is ACGC, AGGG, TAAGGG, or AAGGG.

11. The DNA construct of claim 7, wherein the host cell is *Escherichia coli*.

12. The DNA construct of claim 11, wherein the operator segment is from an *Escherichia coli* recA or trp operator.

13. The DNA construct of claim 11 further comprising a heterologous polypeptide coding sequence operably linked to the heterologous promoter; wherein the polypeptide coding sequence encodes a polypeptide is selected from the group consisting of: a bovine growth factor, a porcine growth factor, a human growth factor, a granulocyte colony stimulating factor (GCSF), erythropoietin (EPO), an insulin, an interleukin, an interferon, and a tissue plasminogen activator (t-PA).

14. The DNA construct of claim 13 wherein the operator segment is from an *Escherichia coli* recA or trp operator.

15. An expression vector comprising a DNA construct for regulating the expression of a polypeptide coding sequence in a transformed bacterial host cell, comprising:
    (a) a heterologous cyanophage N-1 early gene promoter, operably linked to
    (b) an operator segment from an operator native to the host cell, wherein the operator segment is located upstream of the promoter region.

16. The expression vector of claim 15, wherein the host cell is *Escherichia coli*.

17. The expression vector of claim 16, wherein the operator segment is from an *Escherichia coli* recA or trp operator.

18. The expression vector of claim 15, wherein the promoter and the operator segment are connected by a spacer region.

19. The expression vector of claim 18, wherein the spacer region is ACGC, AGGG, TAAGGG, or AAGGG.

20. A bacteria transformed with a heterologous polypeptide coding sequence, wherein the bacteria further comprises a DNA construct for regulating the expression of the heterologous polypeptide coding sequence, wherein the DNA construct comprises:
    (a) a heterologous cyanophage N-1 early gene promoter, operably linked to (b) an operator segment from an operator native to the bacteria, wherein the operator segment is located upstream of the promoter.

21. The transformed bacteria of claim 20, wherein the bacteria is *Escherichia coli*.

22. A culture containing the transformed bacteria of claim 20.

23. A method for producing a heterologous polypeptide in a transformed bacterial host comprising:

(a) stably transforming a bacterial host with a vector containing a heterologous polypeptide coding sequence operably linked to a DNA construct for regulating the expression of the coding sequence, wherein the DNA construct comprises:

(i) a heterologous cyanophage N-1 early gene promoter, operably linked to (ii) an operator segment from an operator native to the host cell, wherein the operator segment is located upstream of the promoter;

(b) culturing the transformed bacteria under conditions that induce the expression of the coding sequence.

24. The method of claim 23, wherein the bacterial host is *Escherichia coli*.

25. The method of claim 23, wherein the heterologous polypeptide is a growth hormone.

26. The method of claim 25, wherein the growth hormone is bovine growth hormone.

* * * * *